Figure 1:
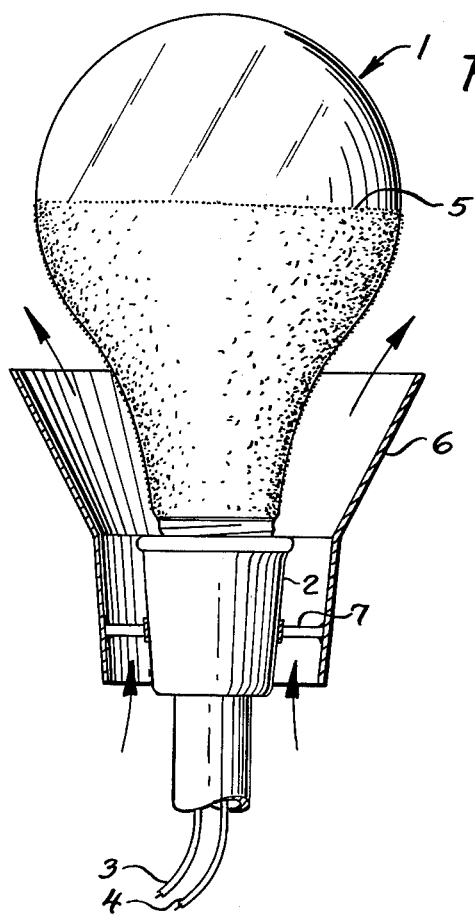

United States Patent [19]

Haensel

[11] 3,930,796
[45] Jan. 6, 1976

[54] CATALYTIC FUME CONTROL DEVICE

[75] Inventor: Vladimir Haensel, Hinsdale, Ill.

[73] Assignee: Universal Oil Products Company, Des Plaines, Ill.

[22] Filed: Sept. 13, 1973

[21] Appl. No.: 396,950

[52] U.S. Cl............ 21/74 R; 23/288 FC; 23/288 J; 252/477 R; 313/110; 313/112
[51] Int. Cl.².... A61L 9/00; B01J 8/02; H01K 1/28
[58] Field of Search............. 21/120, 53, 74 R, 122; 23/288 F, 288 S, 288 FC; 313/110, 112; 240/102, 125, 126; 55/208; 252/477 R; 219/374, 381

[56] References Cited
UNITED STATES PATENTS

| | | | |
|---|---|---|---|
| 1,678,778 | 7/1928 | Harter | 23/288 E |
| 1,864,980 | 6/1932 | Curran | 21/120 |
| 2,539,696 | 1/1951 | Morrison | 21/120 |
| 3,043,977 | 7/1962 | Morowitz | 21/74 R X |
| 3,200,280 | 8/1965 | Thau et al. | 313/110 |
| 3,362,783 | 1/1968 | Leak | 252/477 R X |
| 3,462,632 | 8/1969 | Russi | 313/110 |
| 3,558,958 | 1/1971 | Tartakoff et al. | 313/110 X |
| 3,681,260 | 8/1972 | Foucher | 252/477 R X |
| 3,763,347 | 10/1973 | Whitaker | 252/316 X |
| 3,768,982 | 10/1973 | Kitzner | 23/288 F |

FOREIGN PATENTS OR APPLICATIONS

| | | | |
|---|---|---|---|
| 1,412 | 1882 | United Kingdom | 313/110 |
| 1,141,983 | 1963 | Germany | 252/477 R |

Primary Examiner—Morris O. Wolk
Assistant Examiner—Michael S. Marcus
Attorney, Agent, or Firm—James R. Hoatson, Jr.; Philip T. Liggett; William H. Page, II

[57] ABSTRACT

An electric lamp bulb type of heat furnishing unit is provided with a covering of active oxidation catalyst such that fumes and odors in the confines of a room that are drawn over the catalytic surface will be converted to less objectionable products. A light bulb type of catalyst supporting device is of particular advantage in that it can readily be screwed into a lamp base or other form of current supplying receptacle and, in addition, will provide a hot surface for inducing natural air convection current flow past the catalytic surface. Various types of coatings and/or catalytic wrappings may be used on the bulb to provide any particular type or form of catalytic surface.

8 Claims, 4 Drawing Figures

U.S. Patent  Jan. 6, 1976  3,930,796

CATALYTIC FUME CONTROL DEVICE

The present invention provides a small, portable form of catalytic fume control device which is particularly adapted for a room or other relatively small confined zone. More particularly, there is provided a coating of active oxidation catalyst around a light bulb or a similar form of heat producing unit such that it may be readily mounted in a lamp base or other available electric current supplying receptacle.

Most catalytic converters used in industrial installations for converting oxidizable noxious fumes, or used for effecting the conversion of automobile exhaust gases, prefer relatively high temperature levels of the order of 600° F. or more to provide good conversion efficiencies, although it is realized that with an extended period of time, even at conventional room temperature conditions, there can be catalytically promoted oxidation reactions and conversions. For example, in connection with large commercial processing units, or with drying oven fumes, etc., where objectionable gases and vapors are being released, it is customary to heat the gaseous stream to at least the 600° F. to 700° F. level prior to passing such fumes through catalytic mats such as taught and described in U.S. Pat. Nos. 2,720,494 and 2,658,742. Also in connection with auto exhaust gas converters, it has been deemed desirable to position the catalytic type of reactors closely adjacent the exhaust gas manifolds such that the high temperature of exhaust gas stream will improve the start-up and overall efficiency of the catalytic conversions taking place.

Although a conventional incandescent lamp bulb, of even the 250 to 300 watt size, will not provide a catalyst surface temperature thereon of the order of 600° F., it may readily provide a temperature of the order of 200° F. or more and definitely enhance catalytic conversions of smoke, cooking odors, and other objectionable fumes, particularly in comparison with the rate of reaction which would take place at ambient, room temperature, conditions. It is thus a principal object of the present invention to provide a light bulb type of supporting element for holding a catalytic coating or catalyst covering such that the particular coating will be indirectly heated by means of the electric power being supplied to the bulb from a conventional lamp base or other form of electrical lamp bulb socket.

It may be considered a further object of the present invention to have the convenience and portability of inserting a conventional light bulb, as well as obtain and use the heat output of the bulb to cause natural convection current air flow past the bulb and the catalytic surface therearound.

In one embodiment, the present invention provides a catalytic converter for use in purifying the air in a room or generally small zone, which comprises, an electric lamp bulb adapted to be mounted in an electric current supplying receptacle, and a covering of oxidation catalyst on at least the lower external wall portion of said bulb, whereby the heat from the lamp element therein will maintain a hot catalyst surface to assist in the catalytic conversion of fumes and odors passing thereover in natural convection current flow.

It is not intended to limit the present invention to any one type of coating or covering for the lamp bulb support means, inasmuch as various types of catalytic coatings may be applied directly to the glass surface of the lamp bulb and various methods utilized for effecting the coating of the surface. Also, various types of coverings may be wrapped or otherwise placed directly around the bulb surface in order to obtain the benefit of the heat generation from the lamp bulb. In other words, the term "covering" as used herein shall apply to a coating which is directly applied to the lamp bulb surface or may encompass a wrapped or preformed covering which is adapted to be directly adjacent to the bulb surface.

The oxidation catalyst coating on the bulb or incorporated with a covering may include the metals of Groups I, V, VI and VIII of the Periodic Table, particularly, copper, silver, vanadium, chromium, iron, cobalt, nickel, platinum or palladium, with the components being used singly or in combination with one or more other active components. Of course, for the conversion of fumes and noxious components in a room at ambient conditions, it is preferable to use a highly active noble metal component such that there is more efficient conversion of oxidizable components at the low temperature conditions. The active component(s) may be composited with, or supported by, a suitable refractory inorganic oxide, such as alumina or alumina combined with one or more other refractory inorganic oxides. Typically, the oxide supporting layer will be applied to the bulb surface prior to the coating of an active catalytic component although there may be a mixture made of the refractory metal oxide support material with the active component and the mixture sprayed, dipped, or otherwise coated onto the bulb surface. Also, where deemed desirable, it may be of advantage to provide an etching or other roughening step with respect to the outside surface of the lamp bulb such that there is improved adhesion for the catalytic coating on the bulb surface. Additional methods of applying coatings will be noted more specifically hereinafter.

As an alternative embodiment, there may be the utilization of a catalytically coated refractory gauze, mineral wool, fiber glass, alumina fibers, etc., which may be wound or otherwise wrapped around at least a portion of the bulb surface such that there is direct contact with the bulb and both radiant and conductive heat supplied to the catalytic wrapping. Again, preferred oxidation catalysts which are impregnated on the refractory support material will be those types of catalysts which are highly active and will serve to effect sufficient conversion of combustible products at ambient temperature or at such temperature that will be obtained from the lamp bulb heating.

In still another embodiment, there may be the utilization of a coated metal screening, thin sheet metal material, or a foil-like material such as aluminum foil, and the like, which in turn is directly coated. For example, aluminum foil may be heated to a high temperature to provide an oxidized surface which, in turn, may be coated with a further refractory inorganic oxide coating material and then with a coating of oxidation catalyst component, such as platinum and/or palladium. The foil-like material may be pleated to provide additional surface area but will preferably be wrapped or otherwise placed around the lamp bulb so that it conforms to and is directly adjacent the bulb surface and can obtain conducted heat from the bulb.

In a preferred apparatus arrangement, relatively high wattage light bulbs will be utilized such that there is a relatively large surface area for each conversion device and a relatively high heat output from the incandescent filament within each light bulb to, in turn, provide a relatively high temperature to the bulb surface so as to improve the efficiency of the catalytic conversion taking place on the catalyst surface as fumes pass thereover. The individual bulb members may be provided in a size to be inserted in standard sized sockets or within the conventional oversized sockets, sometimes referred to as "mogul" sized sockets. It is also desirable to provide spaced baffle means, which may be in the nature of a cylinder, or have a frustra-conical configuration, that will encompass the lower portion of the lamp bulb at a spaced distance and enhance natural convection currents in the room air and maintain greater air flow rates upwardly over the bulb surface.

Reference to the accompanying drawing and the following description thereof will serve to illustrate variations in the means for coating or covering the lamp bulb type of conversion device as well as point out additional advantages which may be obtained from the utilization of this type of convenient portable fume oxidation device.

FIG. 1 of the drawing is an elevational view, partially in section, which indicates a construction having a catalytic coating applied directly to the bulb surface.

Figure 2:
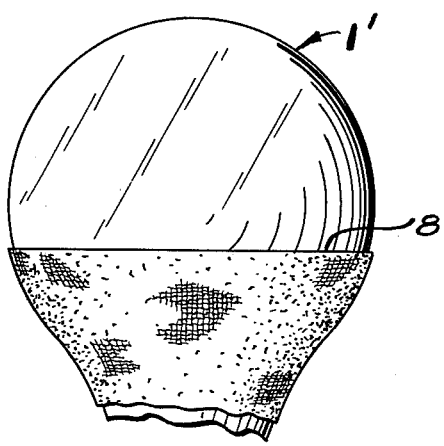

FIG. 2 of the drawing indicates diagrammatically that a catalytic covering may be applied directly over the surface of the lamp bulb.

Figure 3:
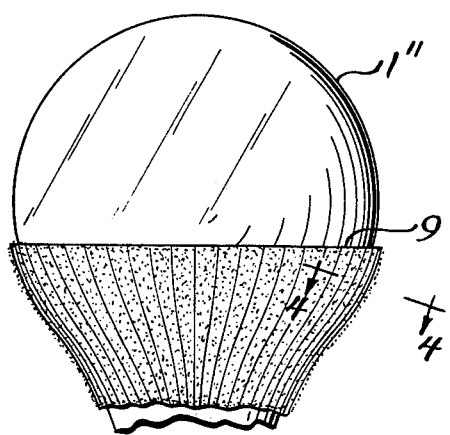
Figure 4:
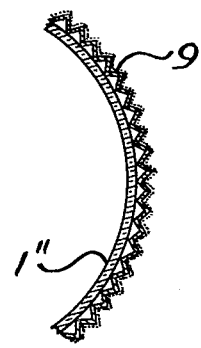

FIGS. 3 and 4 of the drawing indicate diagrammatically still another form of catalytic covering material, such as crimped foil which may be sized and shaped to wrap around at least the portion of the lamp bulb.

Referring now particularly to FIG. 1 of the drawing, there is indicated the utilization of what may be a standard lamp bulb 1, preferably of large size and high wattage, that is adapted to be screwed into an electric current socket 2 that in turn receives suitable electric current by way of lines 3 and 4. At least a lower portion of the lamp bulb 1 is indicated as being catalytically coated at 5 such that when the lamp bulb 1 is turned on by being supplied with electrical power there will be a relatively high surface heating provided for the coating 5 which will permit the latter to effect relatively efficient catalytic conversion of all oxidizable fumes which may pass thereover.

All energized light bulbs automatically tend to cause natural convection currents thereover within any room or any other confined space; however, in order to enhance convection current flow over the surface of the bulb 1 and the coating 5, there may be provided a spaced baffle or wall-like member 6 that encompasses the lower portion of the bulb 1 and the socket means 2 such that the heat from the lamp itself will tend to draw an air stream upwardly through the annular-form passageway between wall 6 and the lower portion of the bulb 1 and cause an annular-form convection current stream to sweep closely across the catalytic surface 5. The wall means 6 may be supported by rods or bar means 7 attached to the lower socket member 2 or it may be supported from suitable leg means connective with a lamp base (not shown) or, in still another instance, the spaced wall 6 may be hung by suitable strap means that would extend over the top portion of bulb 1.

As set forth briefly hereinbefore, it is not intended to limit the present invention to any particular active catalytic component for the surface 5 or be limited to any particular method of effecting the application of the coating over the bulb surface. Generally, it is believed advisable to provide a roughening or acid etching of the bulb surface, such as with hydrofluoric acid, in order to provide a porous surface which will more tenaciously hold the catalytic coating materials. The refractory inorganic oxide support for the catalyst component may be sprayed, dipped or otherwise applied to the roughened surface and as heretofore noted may comprise various types of refractory materials. Reference may be made to U.S. Pat. No. 3,565,830 to provide various teachings for the application of refractory base coatings, as well as for the active catalytic coating; however, still other methods and materials may well be utilized such as taught in the voluminous prior patent art pertaining to this subject matter. For example, U.S. Pat. No. 3,409,390 provides a teaching where calcium, strontium, and barium may be composited with alumina whereby to provide an improved heat resistant catalyst support material. In carrying out the calcining and/or reducing step for producing the catalytic coating directly on the bulb surface, it will, of course, be necessary to limit the calcining and/or reducing temperature to the order of 250° to 300° C. or to whatever will be the maximum limit for the glass bulb. However, in order to obtain the largest crystallite sizes and greatest porosity or surface area for the refractory base material, it is of advantage to use the maximum temperature allowable for the bulb surface.

With reference to FIG. 2 of the drawing, there is indicated a bulb 1' with catalytic covering means 8. Such covering means may comprise a high temperature resistant gauze or fabric, such as may be made from fiber glass, mineral wools, asbestos fibers, alumina fibers, and the like. Actually, alumina fibers as elongated single strands such as prepared under the teachings of U.S. Pat. No. 3,632,709, could be wound around the bulb 1' or could be woven into a fabric such as indicated at 8.

Regardless of the form of temperature resistant covering, such material may be impregnated with a suitable active oxidation catalyst of the type heretofore described by various methods to result in an active surface available for the conversion of fumes which are passed thereover. In addition, reference may be made to U.S. Pat. No. 3,560,408 which sets forth the utilization of mineral fibers and the catalytic activation of such fibers for fume oxidation purposes. Although the present FIG. 2 indicates bulb means 1' to be merely covered on the lower portion thereover, it is to be understood that within the scope of the present invention the bulb means may be entirely covered with a suitable active refractory material whereby maximum utilization is made to the heated bulb surface to in turn provide a maximum surface area to effect conversion of noxious fumes within the confined zone.

With reference to FIGS. 3 and 4 of the drawing, there is indicated a lamp bulb means 1'' having a partial covering 9 which may comprise a foil-like material adapted to conform with and be positioned adjacent to the bulb surface so as to have maximum heating from the bulb. The covering 9 will, in turn, have an active catalytic coating such as described in connection with FIG. 1 of the drawing where there is a first coating of a refractory oxide material in turn impregnated with an active catalytic component or, alternatively, there may be a composite of refractory inorganic material and a catalytic component intermixed therewith applied to the foil-like material. As a specific example, aluminum foil may be heated to provide a roughened surface, at least partially in the aluminum oxide state, that can be sprayed, dipped, or otherwise coated to effect the final catalytic composite on its exterior surface.

In connection with the embodiments of both FIGS. 2 and 3, it may be noted that there is some advantage to utilizing separate covering materials in that such materials can be preconstructed and precoated at suitable oxidation and/or reduction conditions so as to obtain the most optimum catalytic state for the resulting surface of the covering material, with such coating being perhaps more active than that applied directly to the surface of the lamp bulb. In any event, for all of the embodiments there will be at least partially covering of the bulb surface to provide a desirable form of catalytic device which is of a portable nature and at the same time is inherently heated from the normal heat output of the light bulb supporting member.

From the foregoing descriptions relating to modifications in construction and design, it is apparent that still further designs and arrangements may be made utilizing the lamp bulb type of support member which, in turn, provides the desired contact surface in a heated state to enhance catalytic conversion conditions particularly when compared to that which would be obtained at normal room temperature without any external heating means whatever. Regardless of the design and arrangement, it is a particular feature of the present invention to utilize conventional or special light lamp bulb means which can readily be screwed or otherwise mounted into a conventional type of electrical receptacle means and, in turn, provide the maximum ease in mobility and interchangeability with respect to location in any room or confined space. Of course, where desired, a plurality of catalyst covered bulb elements may be utilized in a multiple socket electrical outlet or a plurality of separate sockets each of which having a catalytically coated light bulb means may be used within the same room or confined space.

I claim:

1. A catalytic converter for use in purifying air in a room or generally small zone, which comprises an electric lamp bulb adapted to be mounted in an electric current supplying receptacle and having on at least a portion of its external surface a covering of a refractory inorganic material and an oxidation catalyst comprising at least one metal of Groups I, V, VI and VIII of the Periodic Table, whereby the heat from the bulb will maintain a hot catalyst surface to assist in the catalytic conversion of fumes and odors passing over the bulb in natural convection current flow.

2. The catalytic converter of claim 1 further characterized in that a separate wall means is held in a spaced position around at least the lower portion of said lamp bulb to provide an annular space therebetween and enhance convection air stream flow in such annular space.

3. The catalytic converter of claim 1 further characterized in that said electric lamp bulb is provided with a threaded end and is adapted to be inserted into a threaded electric current supplying receptacle.

4. The catalytic converter of claim 1 further characterized in that said covering comprises a mixture of said refractory material and catalyst.

5. The catalytic converter of claim 1 further characterized in that said covering comprises separate layers of said refractory material and said catalyst, the refractory layer tightly encompassing at least a portion of the bulb surface and being coated with the catalyst layer.

6. The catalytic converter of claim 5 still further characterized in that said covering comprises a catalytic coated foil-like material.

7. The catalytic converter of claim 5 still further characterized in that said refractory material comprises wound refractory inorganic fibers.

8. The catalytic converter of claim 5 still further characterized in that said refractory material comprises a fabric type of material in turn formed from heat resistant fibers.

* * * * *